US010632327B2

(12) United States Patent
Panther (10) Patent No.: US 10,632,327 B2
(45) Date of Patent: Apr. 28, 2020

(54) MRI GUIDED RADIATION THERAPY (71) Applicant: SYNAPTIVE MEDICAL (BARBADOS) INC., Bridgetown (BB)

(72) Inventor: Alexander Gyles Panther, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 215 days.

(21) Appl. No.: 15/522,913

(22) PCT Filed: Nov. 4, 2014

(86) PCT No.: PCT/IB2014/065776
§ 371 (c)(1),
(2) Date: Apr. 28, 2017

(87) PCT Pub. No.: WO2016/071733
PCT Pub. Date: May 12, 2016

(65) Prior Publication Data
US 2017/0312545 A1 Nov. 2, 2017

(51) Int. Cl.
A61B 5/055 (2006.01)
A61N 5/10 (2006.01)
(52) U.S. Cl.
CPC .......... A61N 5/1067 (2013.01); A61B 5/055 (2013.01); A61N 5/1049 (2013.01); A61N 2005/1055 (2013.01); A61N 2005/1061 (2013.01)
(58) Field of Classification Search
CPC .... A61N 2005/1055; A61N 2005/1061; A61N 5/1049; A61N 5/1067
See application file for complete search history.

(56) References Cited

U.S. PATENT DOCUMENTS

2005/0197564 A1  9/2005 Dempsey
2006/0238195 A1* 10/2006 Graesslin ........... G01R 33/3621
                                                              324/309
(Continued)

OTHER PUBLICATIONS

Authorized officer: Blaine R. Copenheaver, PCT Search Report and Written Opinion in PCT/IB2014/065776, dated Feb. 26, 2015, 12 pages.

(Continued)

Primary Examiner — Ruth S Smith
(74) Attorney, Agent, or Firm — Fish & Richardson P.C.

(57) ABSTRACT

Some implementations provide a method that includes: placing a human subject on a moveable platform located in a room with a magnetic resonance imaging (MRI) scanner and a radiation therapy machine; moving the platform into a first position such that the human subject is positioned to be imaged by MRI; operating the MRI scanner while the platform is in the first position to obtain an image of the human subject; moving the platform into a second position such that the human subject is in position to receive radiation therapy from the radiation therapy machine; reducing the magnetic field such that the magnetic field at the radiation therapy machine is below a threshold value; and while the platform is in the second position and the magnetic field at the radiation therapy machine is below the threshold value, operating the radiation therapy machine to perform radiation therapy on the human subject.

28 Claims, 8 Drawing Sheets (56) References Cited

U.S. PATENT DOCUMENTS

| | | | |
|---|---|---|---|
| 2007/0156042 A1* | 7/2007 | Unal | G01R 33/286 |
| | | | 600/410 |
| 2008/0009731 A1 | 1/2008 | Maschke | |
| 2009/0080604 A1 | 3/2009 | Shores | |
| 2010/0219834 A1* | 9/2010 | Luedeke | G01R 33/34007 |
| | | | 324/318 |
| 2010/0231215 A1* | 9/2010 | Ma | G01R 33/3403 |
| | | | 324/307 |
| 2011/0118588 A1 | 5/2011 | Kornblau | |
| 2013/0317343 A1 | 11/2013 | Klimenko | |
| 2014/0033432 A1* | 2/2014 | Marle | A61G 7/1057 |
| | | | 5/601 |
| 2014/0275962 A1* | 9/2014 | Foo | A61N 2/002 |
| | | | 600/411 |

OTHER PUBLICATIONS

PCT International Preliminary Report on Patentability in International Appln. No. PCT/IB2014/65776, dated Oct. 20, 2016, 7 Pages.

\* cited by examiner

MRI GUIDED RADIATION THERAPY

BACKGROUND

The present disclosure relates to magnetic resonance imaging and radiation therapy.

SUMMARY

In one aspect, some implementations provide a method that includes: placing a human subject on a moveable platform, wherein the moveable platform is located in a room with a magnetic resonance imaging (MRI) scanner and a radiation therapy machine, the radiation therapy machine including an external beam generator and the MRI scanner including at least one magnet that generates a magnetic field; moving the platform into a first position such that the human subject is positioned to be imaged by the magnetic resonance imaging (MRI) scanner, the first position resulting in at least a portion of the human subject being located inside the magnet of the MRI scanner; operating the MRI scanner while the platform is in the first position to obtain an image of the human subject; moving the platform into a second position such that the human subject is position to receive radiation therapy from the radiation therapy machine; reducing the magnetic field generated by the magnet such that the magnetic field at the radiation therapy machine is below a threshold value; and while the platform is in the second position and the magnetic field at the radiation therapy machine is below the threshold value, operating the radiation therapy machine to perform radiation therapy on the human subject.

Implementations may include one or more of the following features. Reducing the magnetic field of the magnet may include turning off the magnet such that the magnetic field generated by the magnet at the radiation therapy machine is substantially zero during the radiation therapy. The magnet and the radiation therapy machine may be separated by less than 5 m. The magnetic field generated by the magnet is at least 0.1 Tesla to obtain the image of the human subject. The threshold value is no more than 1 Gauss. The threshold value is no more than 60% of a strength of the magnetic field during magnetic resonance imaging at the radiation therapy machine.

The method may additionally include reducing the magnetic field generated by the magnet while moving the platform into the second position such that the human subject is positioned to receive the radiation therapy from the radiation therapy machine.

The method may further include ramping up the magnetic field generated by the magnet at completion of the radiation therapy.

The method may further include: moving the platform from the first position into the second position while fixing a region of interest of the human subject relative to the platform. The region of interest may include a head region. Operating the radiation therapy machine may include operating an external beam generator and a collimator to generate a radiation beam targeting at the region of interest. Operating the radiation therapy machine to perform radiation therapy may include operating the radiation therapy machine to perform external radiation beam therapy. Operating the radiation therapy machine to perform radiation therapy may further include using a fluoroscopic device to obtain fluoroscopic images of the human subject at the region of interest. Operating the radiation therapy machine to perform radiation therapy may further include fusing the MRI image with the fluoroscopic images to facilitate targeting the radiation beam at the region of interest. Fusing the MRI image on the fluoroscopic images includes aligning the MRI image with the fluoroscopic images by virtue of fixing the region of interest with respect to the platform. Fusing the MRI image on the fluoroscopic images may include using fiducial markers that are visible in both MRI and fluoroscopy. Operating the MRI scanner to obtain the image of the human subject may include operating the MRI scanner to obtain a 3-dimensional image of the human subject at the region of interest. Operating the MRI scanner to obtain the image of the human subject may include operating the MRI scanner to obtain a multi-slice image of the human subject at the region of interest.

In another aspect, some implementations provide a computer-assisted method that includes: placing a human subject on a moveable platform, wherein the moveable platform is located in a room with a magnetic resonance imaging (MRI) scanner and a radiation therapy machine, the radiation therapy machine including an external beam generator and the MRI scanner including at least one magnet that generates a magnetic field; moving the platform into a first position such that the human subject is positioned to be imaged by the magnetic resonance imaging (MRI) scanner, the first position resulting in at least a portion of the human subject being located inside the magnet of the MRI scanner; operating the MRI scanner while the platform is in the first position to obtain an image of the human subject; moving the platform into a second position such that the human subject is position to receive radiation therapy from the radiation therapy machine; reducing the magnetic field generated by the magnet such that the magnetic field at the radiation therapy machine is below a threshold value; and while the platform is in the second position and the magnetic field at the radiation therapy machine is below the threshold value, operating the radiation therapy machine to perform radiation therapy on the human subject.

Implementations may include one or more of the following features. Reducing the magnetic field of the magnet may include turning off the magnet such that the magnetic field generated by the magnet at the radiation therapy machine is substantially zero during the radiation therapy. The magnet and the radiation therapy machine may be separated by less than 5 m. The magnetic field generated by the magnet is at least 0.1 Tesla to obtain the image of the human subject. The threshold value is no more than 1 Gauss. The threshold value is no more than 60% of a strength of the magnetic field during magnetic resonance imaging at the radiation therapy machine.

The method may additionally include reducing the magnetic field generated by the magnet while moving the platform into the second position such that the human subject is positioned to receive the radiation therapy from the radiation therapy machine.

The method may further include ramping up the magnetic field generated by the magnet at completion of the radiation therapy.

The method may further include: moving the platform from the first position into the second position while fixing a region of interest of the human subject relative to the platform. The region of interest may include a head region. Operating the radiation therapy machine may include operating an external beam generator and a collimator to generate a radiation beam targeting at the region of interest. Operating the radiation therapy machine to perform radiation therapy may include operating the radiation therapy machine to perform external radiation beam therapy. Operating the radiation therapy machine to perform radiation therapy may further include using a fluoroscopic device to obtain fluoroscopic images of the human subject at the region of interest. Operating the radiation therapy machine to perform radiation therapy may further include fusing the MRI image with the fluoroscopic images to facilitate targeting the radiation beam at the region of interest. Fusing the MRI image on the fluoroscopic images includes aligning the MRI image with the fluoroscopic images by virtue of fixing the region of interest with respect to the platform. Fusing the MRI image on the fluoroscopic images may include using fiducial markers that are visible in both MRI and fluoroscopy. Operating the MRI scanner to obtain the image of the human subject may include operating the MRI scanner to obtain a 3-dimensional image of the human subject at the region of interest. Operating the MRI scanner to obtain the image of the human subject may include operating the MRI scanner to obtain a multi-slice image of the human subject at the region of interest.

In yet another aspect, some implementations provide an magnetic resonance imaging (MRI) guided radiation therapy system, the system including: an magnetic resonance imaging (MRI) scanner including a magnet configured to generate a magnetic field; a radiation therapy machine located within 5 m of the MRI scanner; a platform configured to transport a human subject from a first position in which at least a portion of the human subject is placed in the magnet to obtain an magnetic resonance image thereof to a second position in which the portion of the human subject is placed in the radiation therapy machine to receive a radiation therapy while the magnetic field at the radiation therapy machine has been reduced below a threshold value.

Implementations may include one or more of the following features. The magnet may be configured to generate a magnetic field at least 0.1 Tesla to obtain the image of the portion of the human subject. The threshold value may be no more than 1 Gauss. The threshold value may be no more than 60% of a strength of the magnetic field during magnetic resonance imaging at the radiation therapy machine. The MRI scanner may further includes a head coil. The magnet of the MRI scanner may include a cryogen-free magnet.

The radiation therapy machine includes an external beam generator and a collimator to generate a radiation beam targeting at portion of the human subject. The radiation therapy machine may be configured to provide external beam therapy.

The platform may include a patient table to which the portion of the human subject is rigidly fixed during transportation from the first position in the magnet to the second position in the radiation therapy machine. The platform may be rotatable over an angular range and may be moveable in more than one spatial direction.

BRIEF DESCRIPTION OF THE DRAWINGS

Embodiments will now be described, by way of example only, with reference to the drawings, in which.

DETAILED DESCRIPTION

Radiation oncologists generally prefer to use magnetic resonance-guidance for radiation therapy systems. However, the high magnetic fields of magnetic resonance imaging (MRI) systems can disturb the operation of the external beam generators (e.g., linear accelerators) of the radiation therapy system. In some implementations, the magnetic field of the MRI magnet is reduced or turned off when the radiation therapy is initiated so that the disturbance caused by the magnet to the radiation therapy system may be non-existent during radiation therapy. In this case, the MRI system can be located near the radiation therapy machine, which may allow the human subject to be expeditiously transported from the MRI scanner to the radiation therapy system on the same platform in the same room. This may allow imaging to be performed immediately before the radiation therapy, thereby yielding up-to-date MRI images of the human subject at the region of interest.

Figure 1:
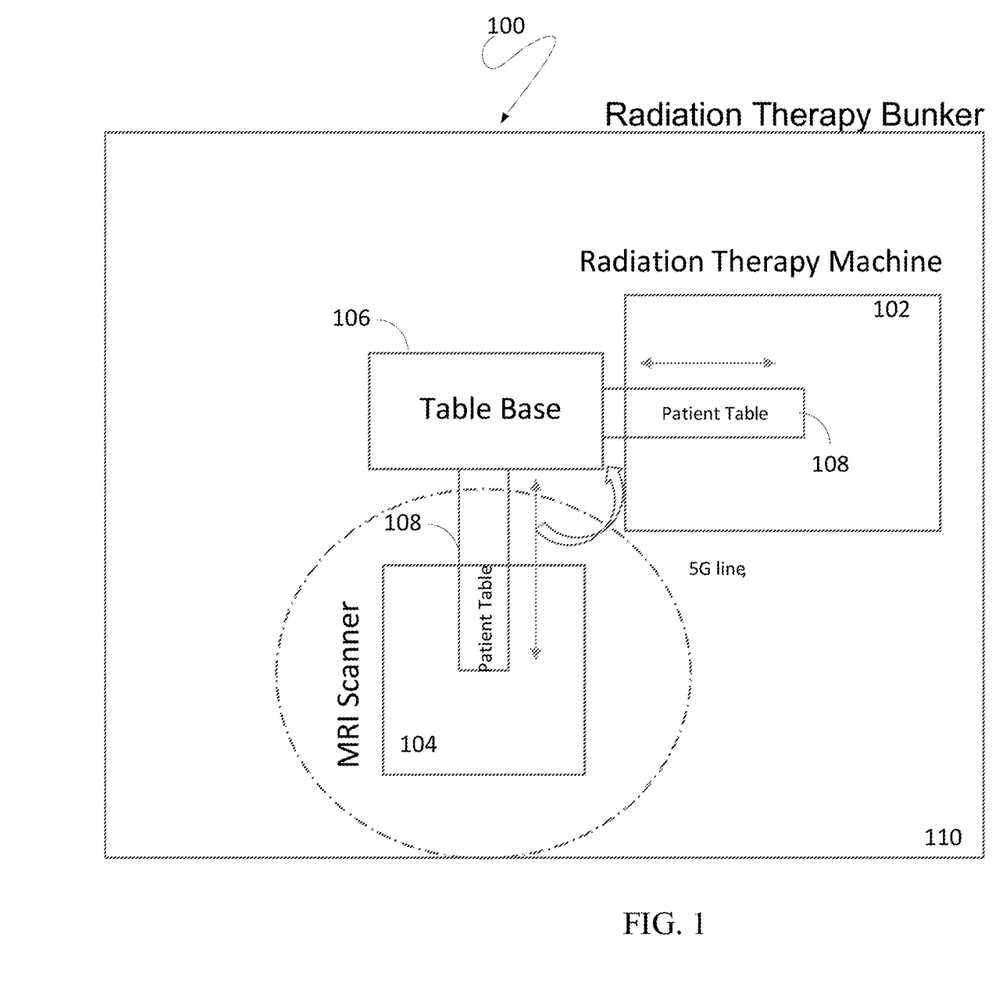
FIG. 1 shows an example of a system including a radiation therapy machine and a magnetic resonance imaging (MRI) scanner.

FIG. 1 shows a top-down view of an example of a system 100 including a radiation therapy machine 102 and a MRI scanner 104 adjacent to each other for MRI guided radiation therapy. As illustrated, system 100 is housed in radiation therapy bunker 110. Radiation therapy machine 102 may include an external beam generator, such as a linear accelerator (LINAC) and a multileaf collimator (MLC). The external beam generator may generate a radiation beam, such as an X-ray beam, targeted at a particular region of a human subject.

MRI scanner 104 may include a magnet, such as a solenoid magnet with an inner bore to house a human subject for imaging. The magnet may have a magnetic field strength from 0.1 Tesla to 7 Tesla for magnetic resonance imaging. The magnet may be a liquid cryogen-free superconducting magnet. For example, MRI magnet may be cooled with a cold-head helium compressor that is used to cool a supporting structure that the superconducting wires are wrapped around. This may allow the magnet to be cooled to a temperature below the critical point of a superconducting wire without the use of liquid cryogens such as liquid helium. A liquid cryogen-free magnet enables operators to manipulate the magnetic field without the need to replenish the cryogen liquid or the risk of quenching the magnet. As a result, an operator may be able to readily reduce or turn off the magnetic field generated by the magnet.

MRI scanner 104 may also include a local coil to image a region of interest of a human subject. In some instances, the local coil may include a head coil for imaging the head region of a human subject. For example, the close proximity of a local coil may provide superior signal-to-noise performance to improve sensitivity or to increase frame rate of a magnetic resonance imaging procedure.

The radiation therapy machine 102 and the MRI scanner 104 are located within the same room. For example, the radiation therapy machine 102 and MRI scanner 104 are located within a radiation therapy bunker, which may be a room that includes radiation shielding and appropriate geometric design to limit the dose of radiation that may be experienced outside of the room. The radiation therapy machine 102 and MRI scanner 104 are positioned at an angle relative to each other. The angle may be a right angle or other configurations. In some instances, radiation therapy machine 102 and MRI scanner 104 can be placed facing each other.

In the illustrated example, the radiation therapy machine 102 is placed such that the machine 102 is outside of the 5 Gauss line of the magnet when the MRI scanner is operated for imaging. This may insure that the radiation therapy machine 102 is not physically attracted to the MRI scanner 104 while the MRI scanner 104 is operated for imaging. In some instances, radiation therapy machine 102 may be placed even closer to MRI scanner 104. When the MRI scanner is not being used for imaging, and when the radiation therapy machine 102 is being operated for treatment, the magnet of the MRI scanner 102 is turned down or off such that the magnetic field generated by the magnet does not affect the operation of the radiation therapy machine 102. For example, the radiation therapy machine 102 and the MRI scanner 104 may be placed relative to each other such that the radiation therapy machine 102 is located outside of the 1 Gauss line when the magnet of the MRI scanner 104 is turned down or off, which may be sufficient to prevent an undesirable effect of the magnetic field on the radiation therapy machine 102 while the radiation therapy machine is being used for treatment. In general, the radiation therapy machine 102 and MRI scanner 104 are placed such that the magnetic field intensity at the radiation therapy machine 102 when the magnet of the MRI scanner is turned down (or off) is below a threshold level, such as the radiation therapy machine's manufacturer's recommended maximum level of the ambient magnetic field during treatment.

System 100 further includes a platform, such as a patient table 108 and a table base 106 on which the patient table 108 is positioned. Patient table 108 is rotatable on table base 106. Patient table 108 is slidable into the MRI scanner 104 or into radiation therapy machine 102. In some implementations, the platform may be rotatable over an angular range and is moveable in more than more spatial directions. In one example configuration, the platform may be rotatable 360°. In another example configuration, the platform may be moveable in three orthogonal spatial directions. In some implementations, the platform may incorporate a computerized motor that can be programmed by a computer to perform the rotations and translations.

Figure 2A:
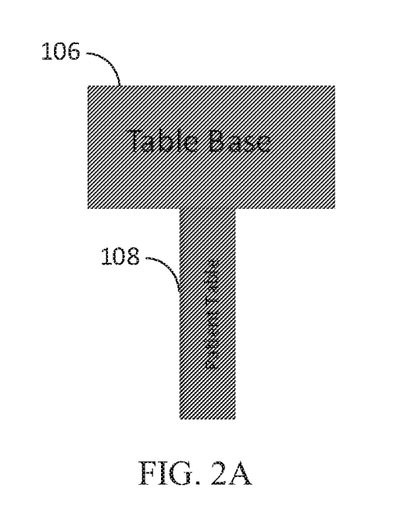
FIGS. 2A-2D illustrate various steps for moving a patient table from a first position in the MRI scanner to a second position in the radiation therapy machine.

Referring now to FIGS. 2A-2D, the operation of patient table 108 is now explained in detail. Initially, patient table 108 is placed in a first position on table base 106. As illustrated in FIG. 2A, this first position refers to the position for patient table 108 to be inserted into, for example, the inner bore of the solenoid magnet of the MRI scanner 104. In this position, a human subject lying on patient table 108 may receive an MRI scan, for example, of the head region. MRI images from this position will be coregistered with respect to patient table 108.

Figure 2B:
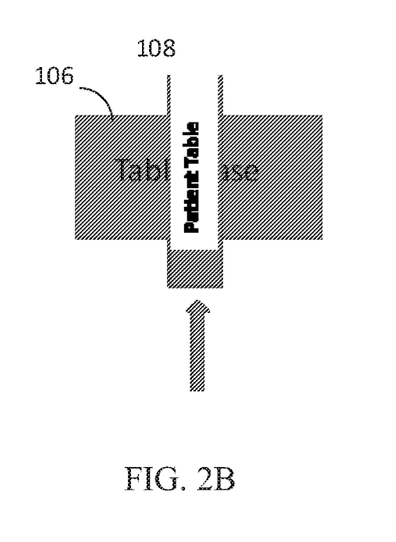

When the magnetic resonance imaging is completed, patient table 108 is moved out of the magnet and placed on table base 106, forming a cross with table base 106, as illustrated in FIG. 2B. For illustration purposes, only the cross configuration is shown. In other configurations, an oblique angle may be formed.

Figure 2C:
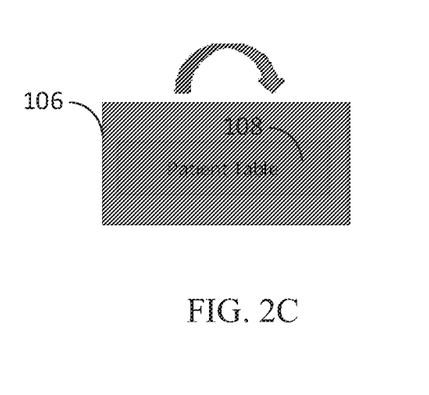

Subsequently, as illustrated in FIG. 2C, patient table 108 is rotated 90° on table base 106 such that patient table 108 is aligned with table base 106. During rotation, the human subject may be immobilized relative to patient table 108 such that the region of interest of the human subject remains fixed relative to patient table 106. The fixation may preserve the coregistration of the region of interest on both MRI scanner 104 and radiation therapy machine 102.

Figure 2D:
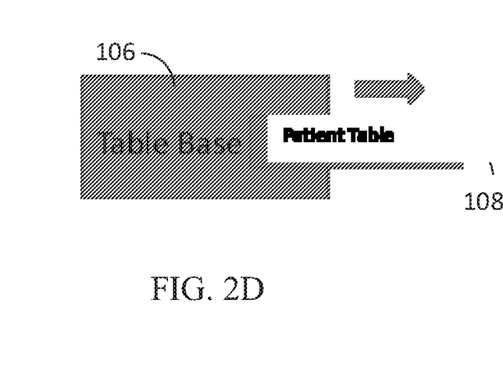

After the rotation, patient table 108 may be slid on table base 106 into radiation therapy machine 102 for the human subject to receive radiation therapy therein.

Accordingly, during use of the system 100, a human subject is placed on the patient table 108. The patient table 108 is moved into a first position such that at least a portion of the human subject is located inside the magnet of the MRI scanner 104 and therefore can be imaged by the MRI scanner 104. The MRI scanner 104 is operated while the patient table 108 is in the first position to obtain an image of the human subject. The patient table 108 is moved into a second position such that the human subject is positioned to receive radiation therapy from the radiation therapy machine 102 and the magnetic field generated by the magnet of the MRI scanner 104 is reduced such that the magnetic field at the radiation therapy machine 102 is below a threshold value (for example, a value at which the magnetic field does not affect the operation of the linear accelerator or other equipment of the radiation therapy machine 102). While the patient table 108 is in the second position and the magnetic field at the radiation therapy machine is below the threshold value, the radiation therapy machine is operated to perform radiation therapy on the human subject.

In the implementations incorporating a computerized motor, the motor can be programmed by a computer to cause patient table 108 to perform rotations and translations so that the human subject can be expediently moved from the MRI scanner 104 to the radiation therapy machine 102. In these implementations, the computer may execute a program to automatically slide patient table 108 away from the MRI scanner 104 (for example, out of the inner bore of the main magnet), rotate the patient table 108 to align it with radiation therapy machine 102, and then slide patient table 108 into radiation therapy machine 102 for the human subject to receive radiation therapy.

Figure 3A:
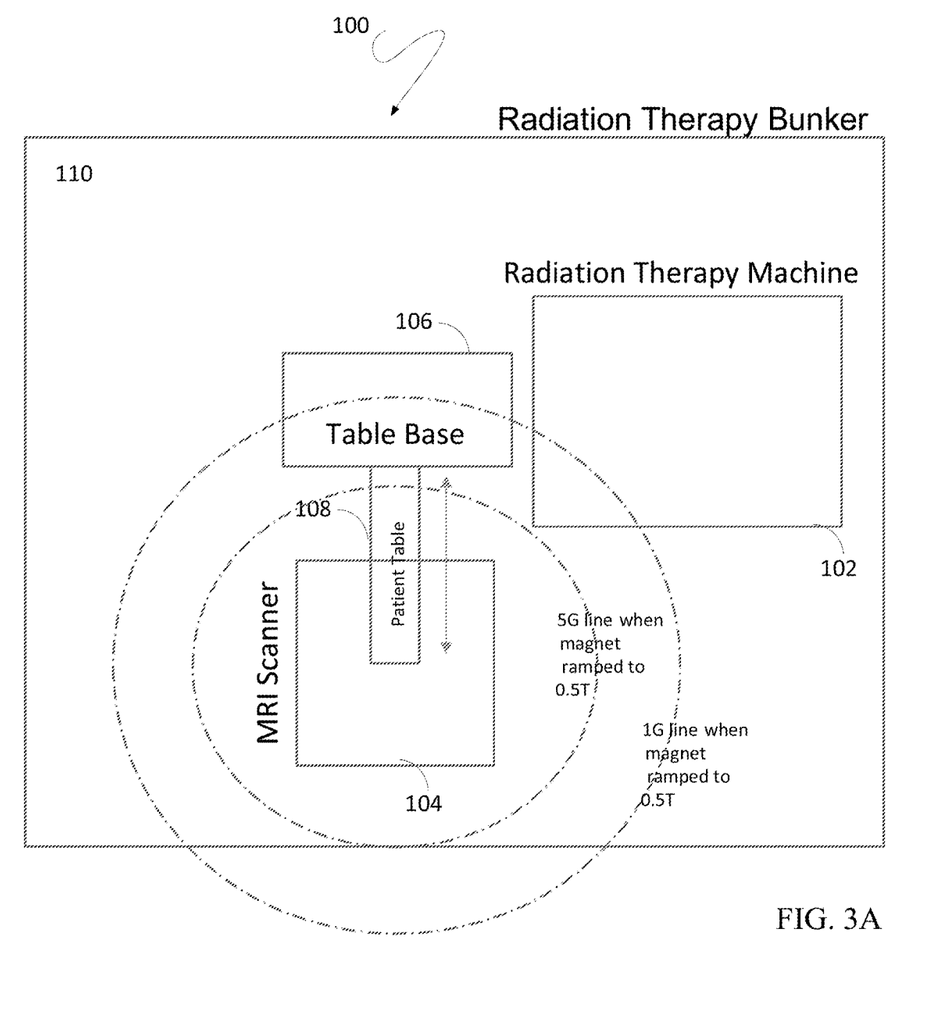
FIGS. 3A-3B show an example of a change in magnetic field intensity of the magnetic field produced by the MRI scanner when switching from imaging using the MRI scanner to treatment using the radiation therapy machine.
Figure 3B:
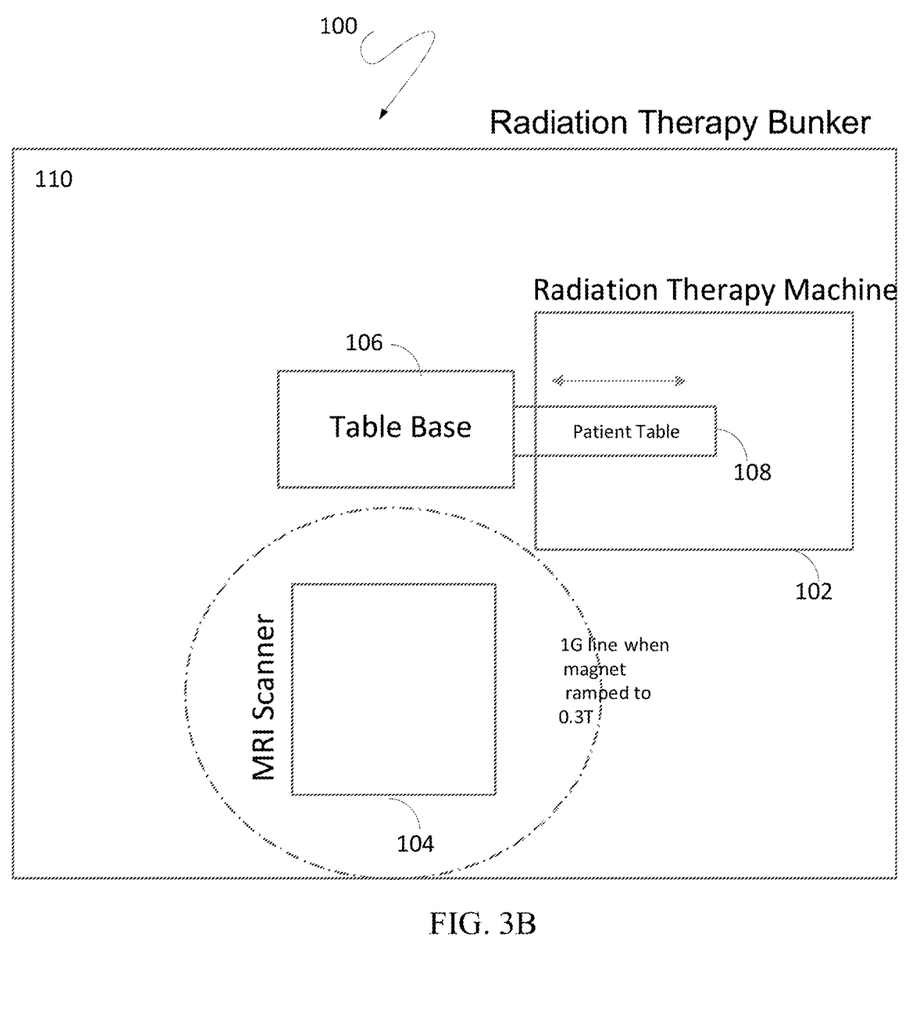

FIGS. 3A-3B show an example of a change in magnetic field intensity of the magnetic field produced by the MRI scanner when switching from imaging using the MRI scanner to treatment using the radiation therapy machine. Referring to FIG. 3A, the patient table 108, with patient (not shown), is placed in a first position in which at least a portion of the patient is located in the MRI scanner 104 for imaging. In this example, the magnet of the MRI scanner is set to 0.5 T when operating the MRI scanner 104 for imaging. As illustrated, the radiation therapy machine 102 and the MRI scanner 104 are arranged relative to each other such that the radiation therapy machine 102 falls outside of the 5 Gauss line when the magnet is set to 0.5 T, but a portion of the radiation therapy machine 102 is within the 1 Gauss line.

If the radiation therapy machine 102 was operated while within the 1 Gauss line, for example, the magnetic field may interact with and disturb the operation of the accelerator on the radiation therapy machine 102. Specifically, the accelerator may include a linear accelerator (LINAC) operable to emit high-energy x-rays to destroy tumors. In more detail, these high-energy x-rays may be generated by using microwave technology to accelerate electrons in a part of the LINAC device called the wave guide. These accelerated electrons are then aimed at a heavy metal target, such as tungsten, to cause plenty of collisions. High-energy X-rays are produced from the target as a result of these collisions. If the LINAC is turned on while within the 1 Gauss (or greater) field, the magnetic field may interfere with the LINAC, to the detriment of the operation of the LINAC. Thus, it is advantageous to reduce or obviate such interference.

Referring to FIG. 3B, to reduce or obviate such interference, the magnet of the MRI scanner 104 is turned down when the radiation therapy machine 102 is to be used in the same radiation therapy bunker 110. In the example shown, the patient table 108 is moved from the first position to a second position in which the patient can receive therapy from the radiation therapy machine 102. Before such therapy is initialed, the magnet of the MRI scanner 108 is turned down, for example, to 0.3 T. This results in the radiation therapy machine 102 being outside of the 1 Gauss line. When the LINAC of radiation therapy machine 102 is operated at this point, the magnetic field intensity may be sufficiently reduced at the radiation therapy machine 102 such that the magnetic field does not interfere with the operation of the LINAC. In some implementations, the magnet of the MRI scanner 108 may be turned off.

The sequence for turning down or turning off the magnet may be initiated while patient table 108 is being moved out of the magnet. In other words, turning down or shutting down the magnet may be pipelined with transitioning patient table 108 from the first position to the second position. In one instance, reducing the magnet from 0.5 T to 0.3 T may take 1-30 minutes, which may overlap with the time for moving patient table 108 out of MR scanner 104 and then into radiation therapy machine 102. In this instance, an operator may reduce the cryogen-free magnet without having to shut down the magnet or replenish liquid helium.

In the implementations incorporating a motor controlled by a computer program, the program may also initiate a sequence to turn down or turn off the main magnet of MRI scanner 104. The program may additionally automatically turn on the external beam generator (for example, a LINAC) of the radiation therapy machine 102 when the interference caused by the main magnet has been substantially suppressed. In some implementations, a magnetic field measuring device such as a Gauss meter may be placed at the perimeter of the radiation therapy machine 102 to detect and measure the fringe field. The measuring device may be coupled to the computer (e.g., the same computer controlling the motorized platform disclosed above in association with FIG. 1). The measuring device may provide digitized input to the computer controlling the sequence of operating the radiation therapy machine. For example, when the fringe field at radiation therapy machine 102 has fallen within a threshold value, the sequence of operating the radiation therapy machine 102 may initiate. Accordingly, the process of transferring the human subject from MRI scanner 104 to radiation therapy machine 102 can be automated.

Figure 4A:
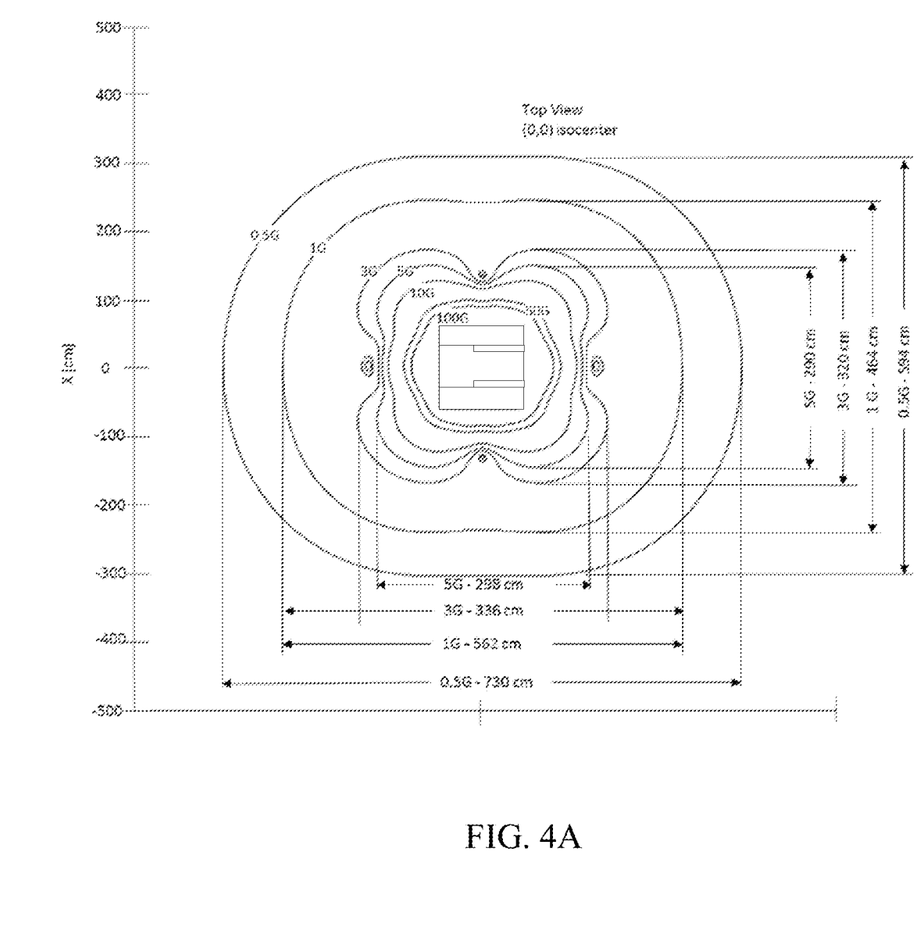
FIGS. 4A-4B show examples of magnetic field plots for an example of a MRI scanner with a 0.5 Tesla magnet and a 0.1665 Tesla magnet, respectively.
Figure 4B:
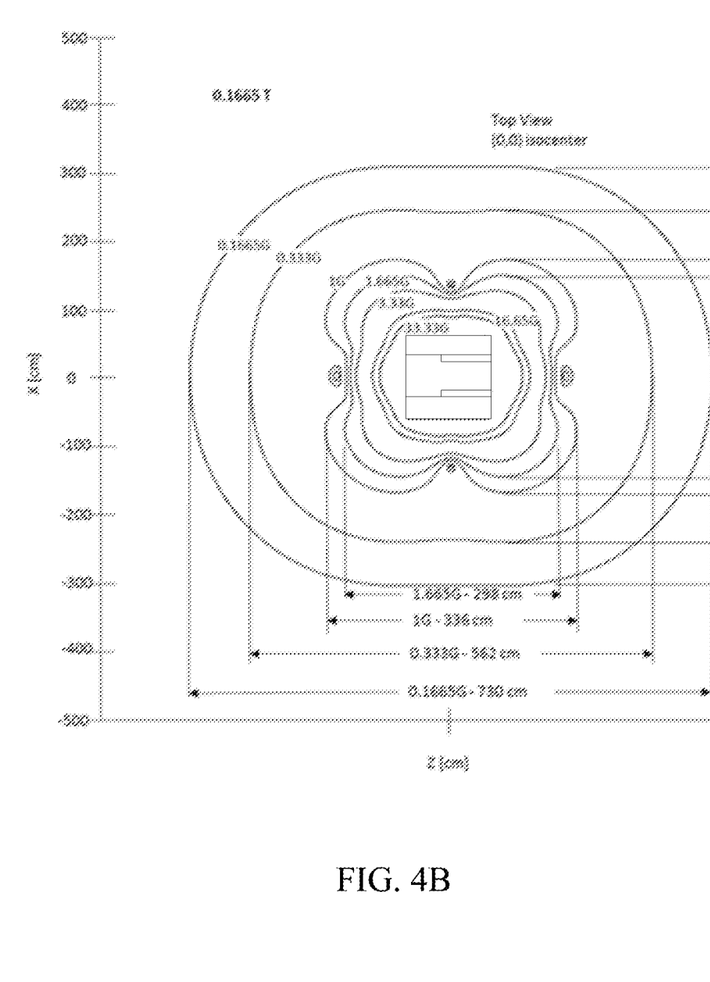

FIG. 4A shows the fringe field for a 0.5 Tesla magnet. As illustrated, the 5 Gauss line is about 1.45 m away from the magnet center while the 1 Gauss line is at 2.32 m away from the magnet. For comparison, FIG. 4B shows the fringe field for a 0.1665 Tesla magnet in which the 1 Gauss line is only 1.68 m away from the magnet center. Because the reduced magnet has fringe field that has shrunk, operating an accelerator for radiation therapy at the same physical distance from the magnet may become less hindered or more advantageous. In some implementations, the separation distance between MR scanner 104 and radiation therapy machine 102 may be no less than 1.68 m. In some implementations, the fringe field at the radiation therapy machine 102 may be no greater than 1 Guass when the LINAC of radiation therapy machine 102 is operated. In some implementations, the fringe field at the radiation therapy machine 102 may be no greater than 60% of the field strength during MRI operation when the magnet is at its full strength.

Figure 5A:
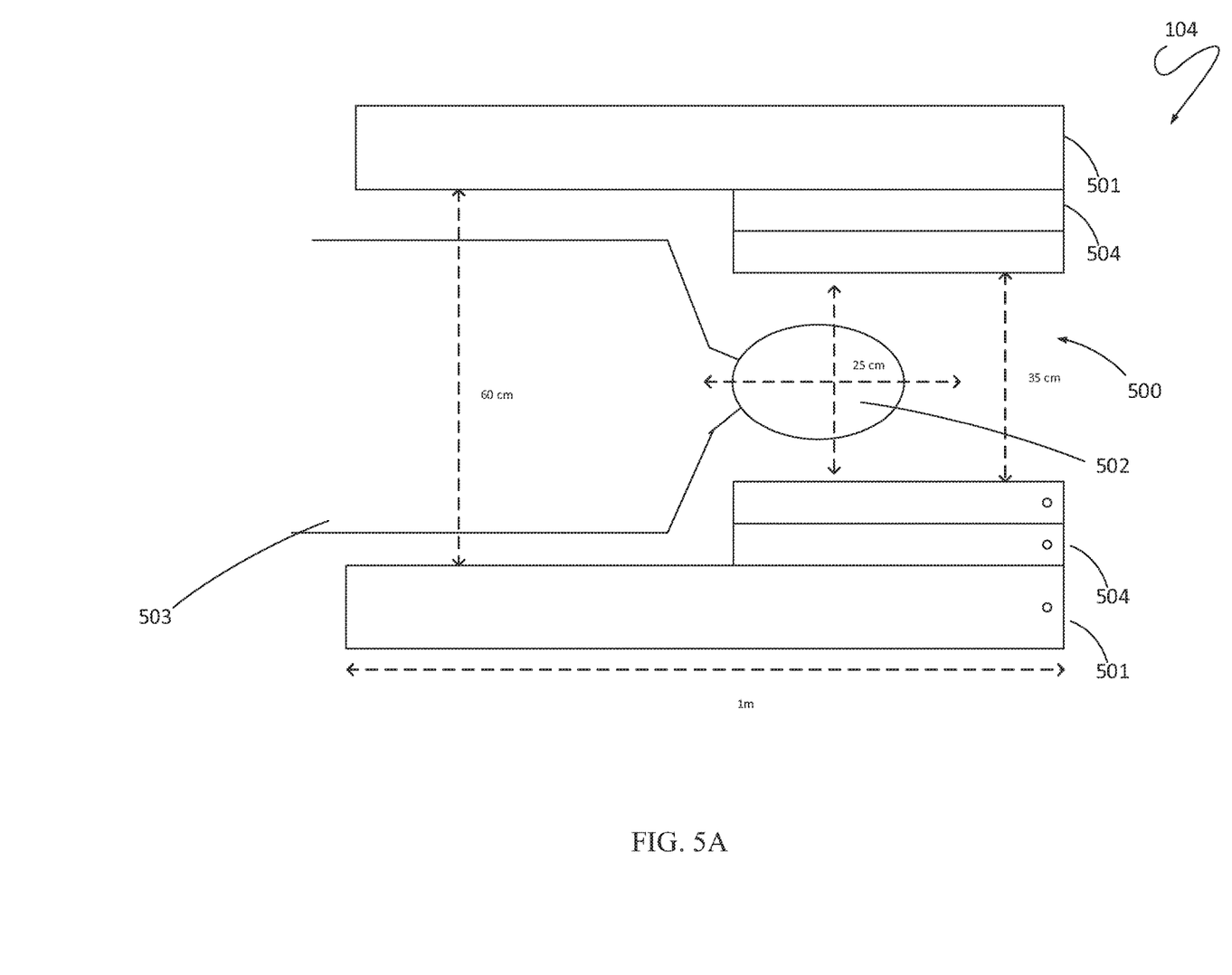
FIGS. 5A-5B illustrate MRI guided radiation therapy for imaging the head region and targeting the same head region using an external radiation beam.

FIG. 5A shows an example of a configuration for imaging the head region 502 of a human subject 503 in MRI scanner 104. This example shows a cross-sectional view of MRI scanner 104 with the sidewalls of solenoid magnet 501 enclosing the inner bore 500. The example dimensions illustrate the relative sizes of the head region and inner bore 500 of solenoid magnet 501. The inner bore 500 of solenoid magnet 501 is 60 cm wide. The diameter of the inner bore 500 can be larger, for example, 70 cm wide. The inner bore 500 may house a coil assembly 504 that includes a gradient coil. The gradient coil may provide a perturbation of the magnetic field to encode MRI signals emitted from head region 502 of the human subject 503. In some implementations, coil assembly 504 may also include a radio-frequency (RF) transmit coil that transmits RF excitation pulses into the head region 502 of the human subject 503. As illustrated, the inner diameter of coil assembly 504 may be reduced to a value that accommodates the insertion of head region 502, but is, for example, less than approximately 60 cm, less than approximately 50 cm, less than approximately 45 cm, less than approximately 40 cm, and less than approximately 35 cm. Coil assembly 504 may be recessed within solenoid magnet 501, such that the patient body (e.g., the shoulders) may be inserted within a broader diameter region (for example, having a diameter of approximately 60 cm) associated with the coil assembly 504, while head region 502 may be inserted within a narrower diameter region associated with the coil assembly 504.

In these implementations, the resulting MRI signals may be received by a head coil (not shown) surrounding head region 502. In other implementations, the head coil may operate as both transmit coil and receive coil. The close proximity of head coil to head region 502 may provide superior signal-to-noise performance.

Figure 5B:
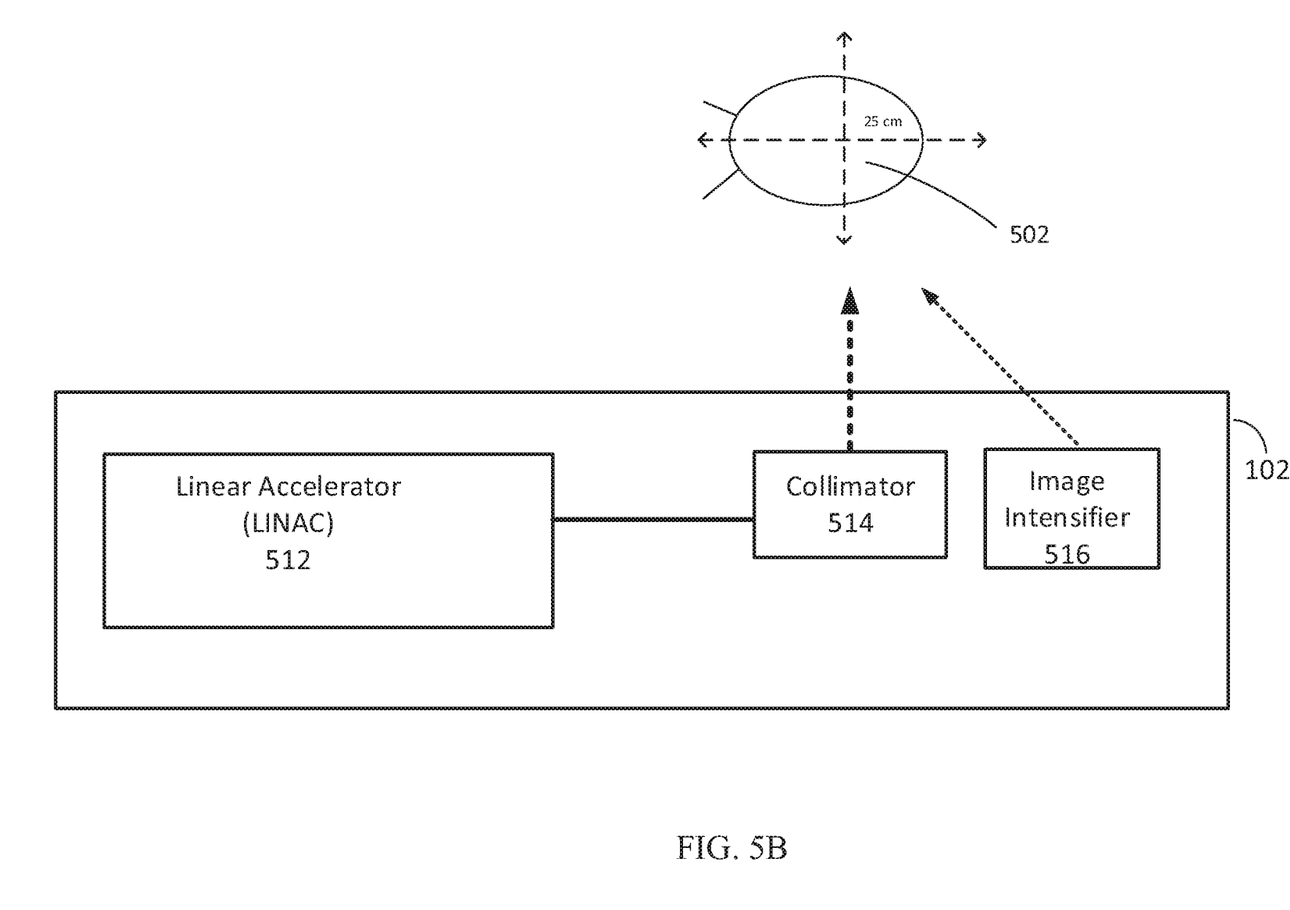

FIG. 5B illustrates an example of a configuration for targeting an external beam therapy, such as a conventional X-ray radiation beam, to the same head region 502 of the human subject. Because the head region 502 of the human subject is secured relative to patient table 108, the coregistration is maintained from the first position in MRI scanner 104 to the second position in radiation therapy machine 102 such that targeting the X-ray radiation beam can take advantage of the magnetic resonance images recently obtained from the same region.

The radiation therapy machine 102 includes a LINAC 512, a collimator 514, and an image intensifier 516. The LINAC 512 includes, for example, a microwave waveguide to accelerate electrons aimed at, for example, a tungsten target. As the high energy electrons collide with the tungsten target, high-energy x-rays are produced. To direct the resulting X-ray radiation beam to the head region 502, collimator 514, such as a multi-leaf collimator (MLC), may be used to collimate the X-ray beam onto a specific target area as guided by, for example, the magnetic resonance images of the head region as obtained from MRI scanner 104 when the human subject was there. In some instances, targeting the X-ray beam at the specific region for radiation therapy may be programmed in accordance with guidance information provided by the magnetic resonance images. Notably, some implementations may include an external beam generator other than LINAC 512. For context, an external beam generator may refer to a radiation therapy apparatus to provide a therapeutic radiation energy source. Example external beam generators may include a LINAC, a proton beam generator, or a gamma knife generator. Example gamma knife generators may include cobalt-60 sources, cesium-137 sources, europium-152 sources, or radium-226 sources.

The image intensifier 516 may be a fluoroscopy device to generate real-time X-ray images of head region 502 to provide intraoperative guidance information for placing the targeting X-ray radiation beams. In some implementations, the fluoroscopic images of head region 502 may provide the general layout, including the boundaries of the skull. The images obtained from MRI scanner 104 immediately before the radiation therapy may be fused with CT or X-ray images. Fusing the MRI image on the fluoroscopic images may include aligning the MRI images with the fluoroscopic images by virtue of fixing the region of interest of head region 502 with respect to patient table 108. Fusing the MRI images on the fluoroscopic images may include using fiducial markers that are visible in both MRI and fluoroscopy. Fusing more than one set of images may also include displaying one set of images superimposed on another set, for example, with a transparency configuration. The images obtained from MRI scanner 104 may provide superior soft-tissue contrast, delineating fine details of the lobular and ventricular structures of the brain encompassing both gray matter and white matter. The images obtained from MRI scanner 104 may include a contrast type tailored to highlight, for example, the boundary of a tumor in the brain. The contrast may include, for example, T1-weighting, T2-weighting, diffusion-weighted, magnetization-transfer weighted, etc. The images obtained from MRI scanner 104 may include a 3-dimensional image of head region 502. The images obtained from MRI scanner 104 may also include a multi-slice image of head region 502.

Upon completion of radiation therapy, LINAC 512 of radiation therapy machine 102 may be turned off and the magnet of MRI scanner 104 may then be ramped up. In some instances, ramping up from a reduced field is more expeditious than ramping up from an off state.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method for providing magnetic resonance imaging guided radiation treatment, the method comprising:

placing a human subject on a moveable platform, wherein the moveable platform is located in a room with a magnetic resonance imaging (MM) scanner and a radiation therapy machine, the radiation therapy machine including an external beam generator and the MM scanner including a single solenoid magnet that encloses an inner bore and generates a magnetic field;

moving the moveable platform into a first position such that at least a portion of the human subject is positioned inside the single solenoid magnet to be imaged by the magnetic resonance imaging (MRI) scanner;

operating the MRI scanner while the moveable platform is in the first position to obtain an MRI image of the human subject;

initiating a transition of the moveable platform from the first position to a second position such that the human subject is positioned outside the single solenoid magnet to receive radiation therapy from the radiation therapy machine;

upon initiating the transition, reducing the magnetic field generated by the single solenoid magnet such that the magnetic field at the radiation therapy machine is below a threshold value; and while the moveable platform is in the second position and the magnetic field at the radiation therapy machine is below the threshold value, operating the radiation therapy machine to perform radiation therapy on the human subject.

2. The method of claim 1 wherein reducing the magnetic field of the single solenoid magnet includes turning off the single solenoid magnet such that the magnetic field generated by the single solenoid magnet at the radiation therapy machine is substantially zero during the radiation therapy.

3. The method of claim 1, wherein the single solenoid magnet and the radiation therapy machine are separated by less than 5 m.

4. The method of claim 1, wherein the magnetic field generated by the single solenoid magnet is at least 0.1 Tesla to obtain the MRI image of the human subject.

5. The method of claim 1, wherein the threshold value is no more than 1 Gauss.

6. The method of claim 1, wherein the threshold value is no more than 60% of a strength of the magnetic field during magnetic resonance imaging at the radiation therapy machine.

7. The method of claim 1, further comprising: ramping up the magnetic field generated by the single solenoid magnet at completion of the radiation therapy.

8. The method of claim 1, further comprising: moving the moveable platform from the first position into the second position while fixing a region of interest of the human subject relative to the moveable platform.

9. The method of claim 8, wherein the region of interest includes a head region.

10. The method of claim 8, wherein operating the radiation therapy machine includes operating an external beam generator and a collimator to generate a radiation beam targeting at the region of interest.

11. The method of claim 10, wherein operating the radiation therapy machine to perform radiation therapy includes operating the radiation therapy machine to perform external radiation beam therapy.

12. The method of claim 10, wherein operating the radiation therapy machine to perform radiation therapy further includes using a fluoroscopic device to obtain fluoroscopic images of the human subject at the region of interest.

13. The method of claim 12, wherein operating the radiation therapy machine to perform radiation therapy further includes fusing the MRI image with the fluoroscopic images to facilitate targeting the radiation beam at the region of interest.

14. The method of claim 13, wherein fusing the MRI image on the fluoroscopic images includes aligning the Mill image with the fluoroscopic images by virtue of fixing the region of interest with respect to the moveable platform.

15. The method of claim 13, wherein operating the MM scanner to obtain the MRI image of the human subject includes operating the Mill scanner to obtain a 3-dimensional image of the human subject at the region of interest.

16. The method of claim 13, wherein operating the MM scanner to obtain the Mill image of the human subject includes operating the Mill scanner to obtain a multi slice image of the human subject at the region of interest.

17. The method of claim 12, wherein fusing the MRI image on the fluoroscopic images includes using fiducial markers that are visible in both the MRI image and fluoroscopy.

18. The method of claim 1, further comprising:
using a Gauss meter placed at a perimeter of the radiation therapy machine to measure the magnetic field; and
automatically turn on a radiation source of the radiation therapy machine when the magnetic field measured by the Gauss meter is below the threshold value.

19. A magnetic resonance imaging (Mill) guided radiation therapy system, comprising:
an magnetic resonance imaging (MM) scanner including a single solenoid magnet that encloses an inner bore and configured to generate a magnetic field inside the inner bore;
a radiation therapy machine located within 5 m of the MM scanner;
a platform;
a Gauss meter placed at a perimeter of the radiation therapy machine and configured to measure the magnetic field; and
a controller in communication with the MM scanner, the radiation therapy machine, the platform, and the Gauss meter,
wherein the platform is configured to transport a human subject from a first position in which at least a portion of the human subject is placed in the single solenoid magnet to obtain an MRI image thereof to a second position in which the portion of the human subject is placed outside the single solenoid magnet and in the radiation therapy machine to receive a radiation therapy while the magnetic field at the radiation therapy machine has been reduced below a threshold value by the controller, and
wherein the controller is configured to:
reduce the magnetic field when the human subject is being transported from the first position to the second position; and
automatically turn on a radiation source of the radiation therapy machine when the magnetic field measured by the Gauss meter is below the threshold value.

20. The MRI guided radiation therapy system of claim 19, wherein the single solenoid magnet is configured to generate a magnetic field at least 0.1 Tesla to obtain the MRI image of the portion of the human subject.

21. The MRI guided radiation therapy system of claim 19, wherein the threshold value is no more than 1 Gauss.

22. The MRI guided radiation therapy system of claim 19, wherein the threshold value is no more than 60% of a strength of the magnetic field during magnetic resonance imaging at the radiation therapy machine.

23. The MRI guided radiation therapy system of claim 19, wherein MRI scanner further includes a head coil.

24. The MRI guided radiation therapy system of claim 19, wherein the single solenoid magnet of the MRI scanner is a cryogen-free magnet.

25. The MRI guided radiation therapy system of claim 19, wherein the radiation therapy machine includes an external beam generator and a collimator to generate a radiation beam targeting at portion of the human subject.

26. The MRI guided radiation therapy system of claim 25, wherein the radiation therapy machine is configured to provide external beam therapy.

27. The MRI guided radiation therapy system of claim 19, wherein the platform includes a patient table to which the portion of the human subject is rigidly fixed during transportation from the first position in the single solenoid magnet to the second position in the radiation therapy machine.

28. The MRI guided radiation therapy system of claim 19, wherein the platform is rotatable over an angular range and is moveable in more than one spatial direction.

* * * * *

UNITED STATES PATENT AND TRADEMARK OFFICE
CERTIFICATE OF CORRECTION

PATENT NO. : 10,632,327 B2
APPLICATION NO. : 15/522913
DATED : April 28, 2020
INVENTOR(S) : Alexander Gyles Panther Page 1 of 1

It is certified that error appears in the above-identified patent and that said Letters Patent is hereby corrected as shown below:

In the Claims

In Column 10, Line 3, Claim 1, delete "(MM)" and insert -- (MRI) --, therefor.

In Column 10, Line 6, Claim 1, delete "(MM)" and insert -- (MRI) --, therefor.

In Column 11, Line 7, Claim 14, delete "(MM)" and insert -- (MRI) --, therefor.

In Column 11, Line 10, Claim 15, delete "(MM)" and insert -- (MRI) --, therefor.

In Column 11, Line 12, Claim 15, delete "Mill" and insert -- (MRI) --, therefor.

In Column 11, Line 14, Claim 16, delete "(MM)" and insert -- (MRI) --, therefor.

In Column 11, Line 15, Claim 16, delete "Mill" and insert -- (MRI) --, therefor.

In Column 11, Line 16, Claim 16, delete "Mill" and insert -- (MRI) --, therefor.

In Column 11, Line 28, Claim 19, delete "Mill" and insert -- (MRI) --, therefor.

In Column 11, Line 30, Claim 19, delete "(MM)" and insert -- (MRI) --, therefor.

In Column 11, Line 34, Claim 19, delete "(MM)" and insert -- (MRI) --, therefor.

In Column 11, Line 40, Claim 19, delete "(MM)" and insert -- (MRI) --, therefor.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*